United States Patent [19]

Connelly, Jr.

[11] Patent Number: 4,496,318
[45] Date of Patent: Jan. 29, 1985

[54] CONVERTERS FOR ORTHODONTIC TREATMENT

[76] Inventor: Harold R. Connelly, Jr., 2499 Main St., Stratford, Conn. 06497

[21] Appl. No.: 379,089

[22] Filed: May 17, 1982

[51] Int. Cl.³ .............................................. A61C 7/00
[52] U.S. Cl. ...................................... 433/14; 433/15; 433/16; 433/17
[58] Field of Search .................... 433/8, 14, 16, 13, 17

[56] References Cited

U.S. PATENT DOCUMENTS

| | | | |
|---|---|---|---|
| 1,323,141 | 11/1919 | Young | 433/14 |
| 2,908,974 | 10/1959 | Stifter | 433/16 |
| 3,128,553 | 4/1964 | Begg | 433/14 |
| 3,134,171 | 5/1964 | Kessler | 433/14 |
| 3,163,933 | 5/1965 | Begg et al. | 433/14 |
| 3,178,822 | 4/1965 | Fogel et al. | 433/8 |
| 3,477,129 | 11/1969 | Rubin | 433/17 |
| 4,212,638 | 7/1980 | Korn | 433/16 |

OTHER PUBLICATIONS

L. F. Andrews, "The Straight-Wire Appliance Origin, Controversy, Commentary", JCO, vol. X, No. 2, pp. 99-114 (Feb., 1976).
G. R. Cadman, "A Vade Mecum for the Begg Technique: Technical Principles", American Journal of Orthodontics, vol. 67, No. 5, pp. 477-512 (May 1975).
G. R. Cadman, "A Vade Mecum for the Begg Technique: Treatment Procedures", American Journal of Orthodontics, vol. 67, No. 6, pp. 601-624 (Jun. 1975).
Wm. Thompson, "Begg and Straight Wire: A combination approach to Treatment", American Journal of Orthodontics, vol. 79, No. 6, pp. 591-608 (Jun. 1981).

Primary Examiner—Robert Peshock
Attorney, Agent, or Firm—Pennie & Edmonds

[57] ABSTRACT

Orthodontic converters for converting straight wire archwire tooth receptacles to light wire appliance system treatment and light wire archwire tooth receptacles to straight wire appliance system treatment. The converters have snap clips for selectively and conveniently attaching and detaching the converter to the tooth receptacle. The converter also includes a cut-out to accept an archwire of the chosen system.

17 Claims, 15 Drawing Figures

CONVERTERS FOR ORTHODONTIC TREATMENT

BACKGROUND OF THE INVENTION

1. Field of the Invention

This invention relates to appliance systems used in orthodontic treatment.

2. Description of the Prior Art

The practice of orthodonitics involves the correction of dental irregularities and malocclusions by the application of forces to the teeth. The orthodontist applies corrective forces to the teeth requiring repositioning by attaching orthodontic appliances to them. These appliances are then connected to each other by a metal archwire. The orthodontist controls the amount and direction of the forces required to effect a repositioning of the teeth by selective bending of the archwire.

Current orthodontic treatment methods employing fixed orthodontic appliances are divided into two broad categories—the light wire method, of which the Begg method is one form, and rectangular wire (or edgewise) method, of which the straight wire method is one form.

The light wire method moves teeth by tipping and torquing the tooth into a new position. In the light wire method, an appliance or archwire receptacle, attached to a tooth, is connected to an archwire at what can be described as a point contact. Corrective force is applied to the tooth through the archwire, but due to the point contact connection between the archwire and the tooth, it is free to rotate and tip. This connection allows the tooth to move easily and large changes in tooth position are accomplished by the use of light forces. However, the freedom of tooth movement makes it difficult to accurately control positioning.

The rectangular wire method uses a more rigid system. A rectangular archwire is positioned in a rectangular slot in a tooth appliance or archwire receptacle. The tooth freedom of movement is limited by the rigid connection between the rectangular archwire and the rectangular receiving slot. A tooth so attached must move along or with the archwire and precise repositioning is possible. However, the rigid connection leads to large frictional forces; therefore, higher forces must be used to counteract the frictional forces and thereby move the tooth. Generally a longer treatment time is required for extensive tooth movement by this method than by the light wire method.

The straight wire technique is a modified rectangular wire system wherein the orthodontist first makes a model of the patient's dental arch. Using this model, he selects rectangular brackets having what he considers to be the proper amounts of torque and/or angulation to precisely reposition the teeth. These appliances are then positioned on the patient's teeth and a straight archwire is placed into the tooth brackets.

Generally speaking, orthodontists practicing in the eastern portion of the United States use light wire treatment systems while western orthordontists use some form of rectangular wire treatment. In our increasingly mobile society it is common for patients undergoing treatment to move from one part of the country to another. The patient may have difficulty obtaining the services of an orthodontist who is willing to continue treatment with the initially-chosen appliance system. Removal of the old system tooth brackets and replacement with those of another system is wasteful and extremely expensive.

Both the light wire and straight wire methods have advantages and disadvantages, as more fully discussed in "Begg and straight wire: A combination approach to treatment" by William Thompson, *American Journal of Orthodontics,* Vol. 79, No. 6, 591–608, June 1981. Generally the Begg light wire technique leads to rapid large movements of teeth with relatively little pain; however, it does not perform fine precision adjustments which are necessary for final tooth interdigitation. On the other hand, the straight wire technique leads to a relatively more accurate final alignment of teeth. However, the straight wire technique is more painful and requires longer treatment time to effect large tooth movements.

Often it is desirable to use Begg appliances for the large tooth movement portion of treatment and then switch to straight wire appliances to "fine tune" tooth adjustment during the final portion of treatment.

Various attempts have been made in the past to design orthodontic appliances that are capable of being utilized to effect both methods of treatment in order to gain the advantage inherent in each.

U.S. Pat. Nos. 3,163,933 and 3,178,822 describe combination one-piece orthodontic appliances having the capability of being used in either the light wire or rectangular wire method. These devices must be used from the beginning of treatment in order to switch from one appliance system to another.

U.S. Pat. No. 4,212,638 describes a combination light wire-rectangular wire orthodontic appliance system which provides the practictioner with means of employing both treatment methods without the necessity of changing tooth brackets during treatment. A bracket is provided which receives a light wire-type archwire. The archwire is secured to the bracket by means of a lock pin positioned in the bracket. An insert for holding rectangular straight wire-type archwires must be attached to the bracket by lock pins. The '638 patent requires the use of a standard "universal"-type tooth bracket to effect the conversion from one method to the other. Existing design brackets may not be used since they lack the necessary lock pin holes. Also, since the lock pins are extremely small, their insertion by an orthodontist presents quite a difficult procedure.

Figures 1, 2, 3:
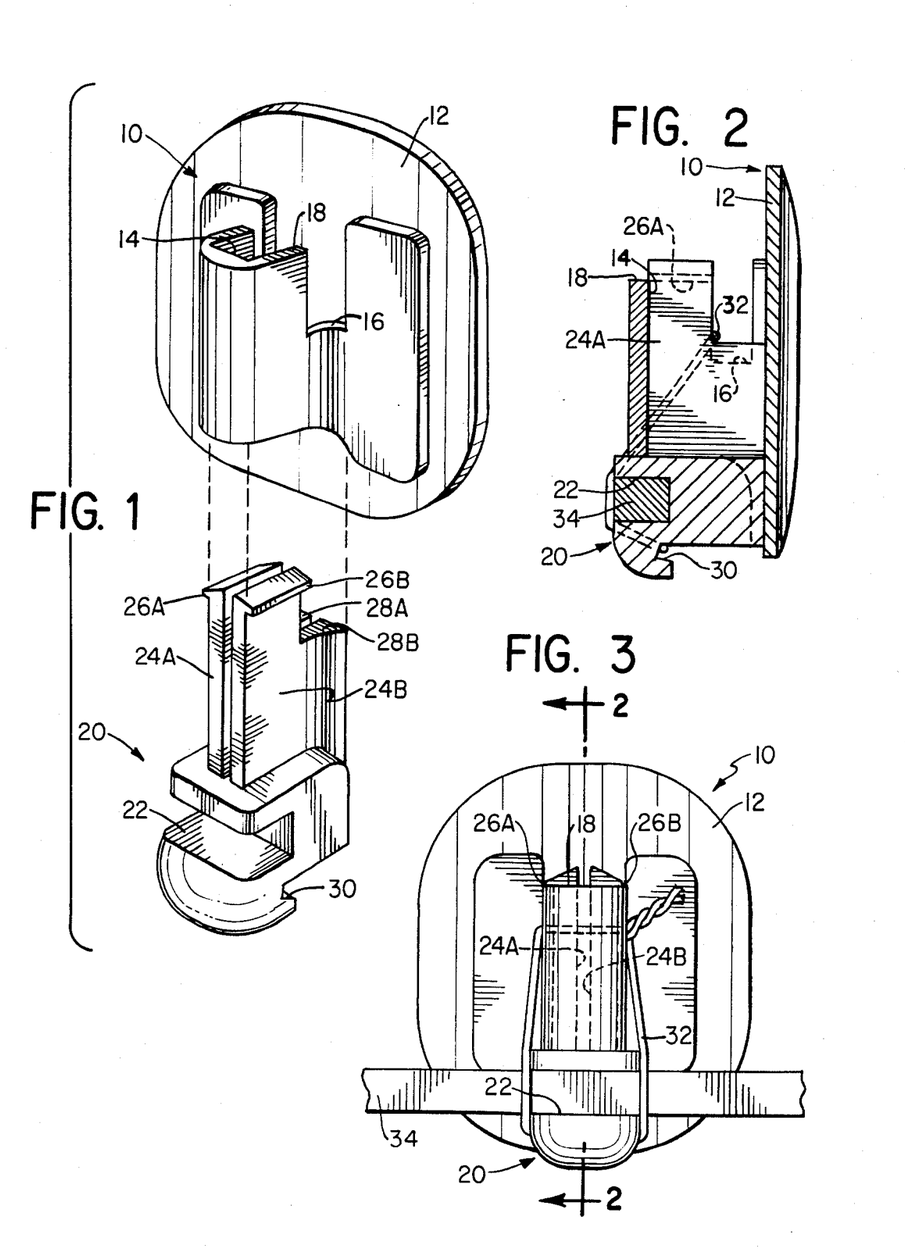
FIG. 1 is an exploded perspective view of an embodiment of the invention positioned for insertion into a known type of tooth bracket.
FIG. 2 is a sectional elevational view of the invention taken along line 2—2 of FIG. 3.
FIG. 3 is a front elevational view of the invention installed in a known light wire-type tooth bracket with a known straight wire-type archwire.
Figures 4, 5:
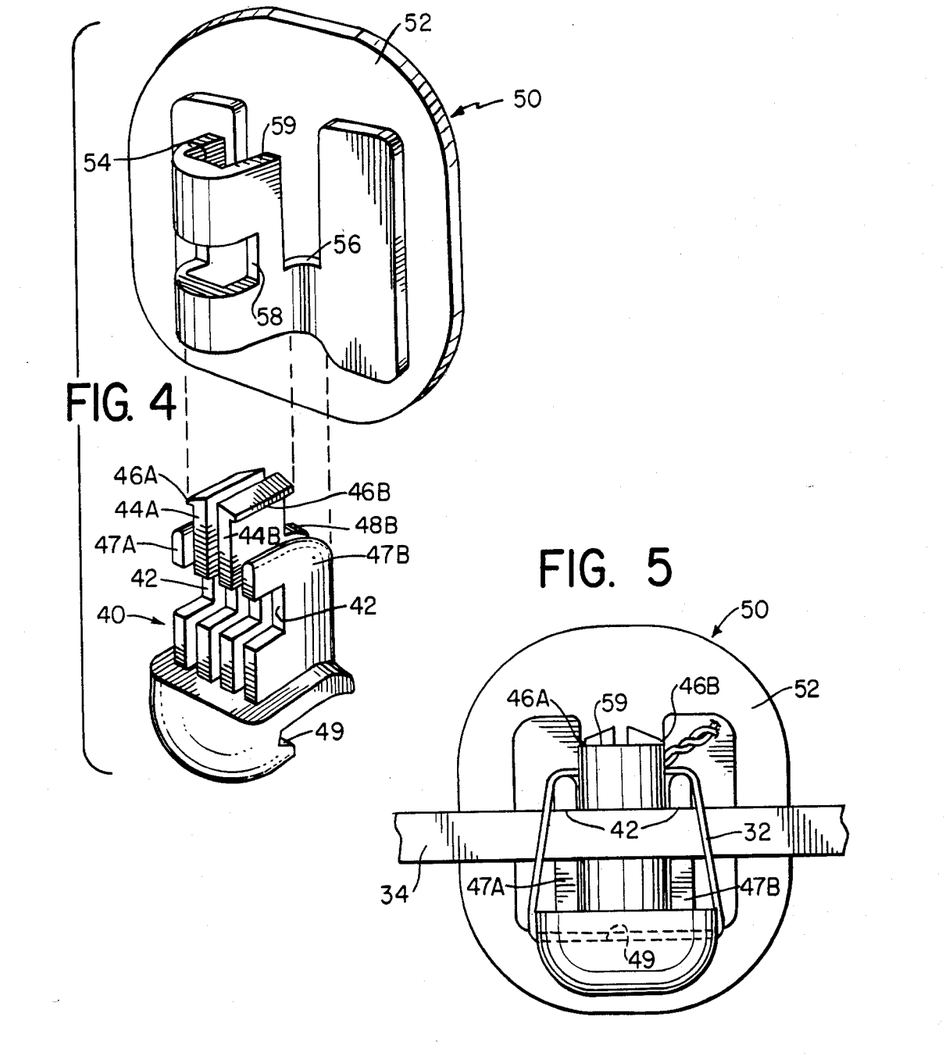
FIG. 4 is an exploded perspective view of another embodiment of the invention prior to insertion into a known archwire-type tooth bracket.
FIG. 5 shows is a front elevational view of the invention shown after installation.

The converter disclosed in the '638 patent does not apply treatment corrective forces along relatively the same line of action for both treatment systems. For example, FIG. 3 shows the use of a light wire-type archwire. The light wire applies its force to the tooth to which it is attached slightly above the horizontal centerline of the bracket. FIG. 4 shows the converter and an attached straight wire-type archwire. The straight wire applies its force well below the horizontal centerline of the bracket.

Although of the above-noted references disclose conversion systems which constitute some form of universal tooth bracket useful only for the specific system disclosed, they cannot be used with common types of brackets presently used in either the straight or light wire systems. A patient who has only standard tooth brackets cannot utilize the advantages inherent in any of the above references. Thus, a patient who moves to another part of the country where his present treatment system is not in vogue may not convert to another system of treatment without removal of his or her old tooth brackets. Replacement of tooth brackets usually is extremely costly.

An orthodontist who already has an existing inventory of tooth archwire receptacles, including brackets, tubes, or sheaths designed for one specific treatment system cannot switch to the other form of treatment system during the course of treatment in order to utilize the advantages inherent in both systems. In order to use both systems for treatment, he must forego use of his present inventory of brackets and purchase an entirely new inventory of the universal brackets and inserts constructed in accordance with the teaching of one of the above references. Common business logic dictates that the patients, or their insurance companies, will eventually assume the cost necessary to acquire the new inventory of tooth brackets through higher orthodontist service fees.

SUMMARY OF THE INVENTION

I have invented an orthodontic converter for adapting a first appliance member associated with an orthodontic treatment system of a first type for use with an orthodontic treatment system of a second type. The converter comprises a second appliance member having a clip means for selective and convenient attachment into the first appliance member. The second member further defined cut-out means for reception of an archwire associated with a second system. The first member may be a light wire orthodontic system archwire receptacles and the second member utilizes a rectangular archwire used in straight wire orthodontic treatment systems. Alternatively, the first member may be a straight wire orthodontic system archwire receptacle and the second member utilizes an archwire used in light wire orthodontic treatment systems.

The cut-out means may be located on the converter such that force by either method of treatment acts along substantially the same line of action. The converter allows an orthodontist to switch from one system of treatment to another system of treatment without the need to replace existing tooth brackets, with either a universal conversion tooth bracket or common brackets of the other treatment system. Different embodiments of my invention fit standard types of light wire and straight wire tooth brackets commonly used by orthodontic practitioners.

In one embodiment of my invention, the converter is designed for insertion into light wire orthodontic appliance system tooth brackets where the bracket has a channel. The converter comprises clip means, preferably snap clip means, adapted for insertion into the bracket channel, and the cut-out is a slot extending generally horizontally across the converter adapted for receipt of a rectangular archwire used in straight wire orthodontic appliance systems. The light wire orthodontic system brackets are then used in straight wire orthodontic treatment by attachment of straight wire components.

In another embodiment of my invention, the converter is designed for insertion into straight wire orthodontic appliance system tooth brackets having a pair of parallel vertical flanges perpendicular to the bracket where each flange is adapted for receipt of a rectangular archwire. This embodiment of the converter comprises a body adapted to fit between the parallel flanges of the tooth bracket, the body having a cut-out notch for receipt of a light wire system archwire and a channel generally extending parallel to the bracket flanges; clip means (preferably snap clip means) for clipping the converter to the tooth bracket flanges; a locking finger having a lug, the locking finger adapted for insertion into the converter channel wherein the finger lug fits over the converter notch for preventing escape of a light wire-type archwire inserted into the notch. The straight wire appliance system tooth brackets are then used for light wire orthodontic treatment by attachment of light wire components.

In a third embodiment of my invention, a converter is designed for use with light wire orthodontic system tooth buccal tubes which have an aperture for insertion of an archwire. This tube is used for molar teeth. This embodiment of the converter comprises clip means adapted for insertion into buccal tube aperture, and the converter cut-out means is an aperture adapted for insertion of rectangular archwire used in straight wire orthodontic systems.

In a fourth embodiment of my invention, the converter is designed for insertion into straight wire rectangular sheath having an aperture adapted for receipt of a rectangular archwire. This type of sheath is used for molar teeth. The converter comprises clip means adapted for insertion into the sheath aperture, and the converter cut-out means is an aperture adapted for receipt of a light wire-type archwire.

Thus the conerters of my invention facilitate use with the brackets, buccal tubes and sheaths that are presently, commonly, in use in present day orthodontics and conversion from one system to another is thereby obviated. Adaptation can be accomplished in minutes, in the orthodontist's office due particularly to the snap clip feature of my invention.

BRIEF DESCRIPTION OF THE DRAWINGS

These and other advantages of my invention may be understood by reference to the following drawings wherein.

DESCRIPTION OF THE PREFERRED EMBODIMENTS

FIGS. 1 through 8 shows embodiments of the invention suitable for use with teeth other than molars, while FIGS. 9 through 14 are suitable for use on molar teeth. FIGS. 1 through 5 and FIGS. 12 through 14 illustrate the preferred component parts of this invention which allow an orthodontist to change from light wire orthodontic appliance systems to straight wire systems. FIGS. 6 through 11 illustrate the component parts of this invention which allow an orthodontist to change from straight wire orthodontic appliance systems to light wire systems.

Referring first to FIGS. 1 through 3, FIG. 1 shows a known type of tooth bracket 10 used by orthodontists in light wire treatment. Bracket 10 has a bracket pad 12 which attaches to the front of a tooth crown during use. Pad 12 is attached to the tooth by means well known in the art, such as by adhesives. Alternatively the pad 12 may be attached to a metal band, not shown. The band, in turn, wraps around the circumference of the tooth. Bracket 10 has a generally U-shaped channel 14. The bracket also has a bracket notch 16 extending perpendicular to the channel. Bracket notch 16 normally contains an archwire (not shown) used in light wire orthodontic systems which provides the necessary force to move the tooth during the orthodontic treatment.

Converter 20 has a slot 22 adapted to hold rectangular archwires normally used in straight wire orthodontic treatment systems. Converter 20 is attached to tooth bracket 10 by clip means such as snap clips 24A and 24B. Clips 24A and 24B are adapted for slidable insertion into bracket channel 14. Insertion of clips 24A and 24B into channel 14 squeezes the clips inwardly while biasing them outwardly away from the center of the channel. Lips 26A and 26B prevent separation of the converter 20 from bracket 10 as the converter seats to its locked position. Once converter 20 is installed, an orthodontist may remove it by squeezing lips 26A and 26B in an inwardly direction, so that the lips clear the top edge 18 of channel 14, while simultaneously separating the converter from the bracket 10.

Lips 24A and 24B have reinforcement means such as flanges 28A and 28B. Converter flanges 28A and 28B prevent rocking of the converter 20 within channel 14 by filling excess space within the channel. Flanges 28A and 28B also add additional material to the clips, which increases converter 20's strength and resistance to either bending or breakage.

Converter 20 also has means to receive auxilliary equipment, such as tie wires and elastic rings used in orthodontic treatment. In FIGS. 1 and 2 the attachment means are shown as groove 30. In FIGS. 2 and 3 tie wire 32 secures a rectangular archwire 34 within converter slot 22. Persons skilled in the art will appreciate that any other attachment means necessary to perform orthodontic treatments may be provided on the converter.

The converter embodiment shown in FIGS. 1 through 3 has converter slot 22, which receives rectangular wire 34. Those skilled in the art of orthodontic treatment will appreciate that the appliance forces exerted on a tooth act through slot 22.

Some orthodontic practitioners feel that the ideal appliance force exertion location on teeth is near the horizontal centerline of the tooth crown. They prefer to have the rectangular archwire slot located subtantially closer to the center of the tooth bracket which is normally located close to the centerline of the crown. Accordingly, FIGS. 4 and 5 show a converter embodiment having a converter slot 42 located substantially closer to the vertical centerline of tooth bracket 50.

Tooth bracket 50 has a pad 52 like that of the bracket shown in FIGS. 1 through 3. Bracket 50 also has a channel 54 similar to that of bracket 10. Bracket notch 56 holds archwires used in the light wire orthodontic appliance system. Bracket 50 also has a bracket slot 58 adapted to provide clearance for converter slot 42.

Referring to FIG. 4 converter 40 is adapted for slidable insertion into bracket channel 54. Clip means, such as snap clips 44A and 44B, retain the converter in channel 54. To prevent separation of converter 40 from bracker 50 the converter clips 44A and 44B have lips 46A and 46B which engage the upper face 59 of bracket 50 after the converter is seated in the bracket. Lips 46A and 46B are squeezed in an inwardly direction and biased in an outwardly direction away from the centerline of the channel 54 when inserted into the channel. An orthodontist may selectively remove the converter 40 by squeezing lips 46A and 46B in an inwardly direction and by simultaneously separating converter 40 from bracket 50.

Converter 40 has strengthening ribs 47A and 47B which also contain the archwire slot 42. Converter ribs 47A and 47B are positioned outside channel 54 of bracket 50 and add strength to the converter and to the combination converter-bracket assembly. These ribs 47A and 47B also increase the area in contact with the rectangular archwire, increasing tip and torque control. The clips 44A and 44B have reinforcement means, such as flanges 48A (not shown and 48B, adapted for insertion into the bracket channel to prevent movement of the inserted converter within the bracket channel and for strengthening the clips. Converter 40 also has attachment means such as groove 49 for attachment of auxilliary equipment, such as tie wires and elastic rings used during orthodontic treatment. In FIG. 5, tie wire 32 passes through groove 49. Tie wire 32 retains rectangular archwire 34 within the converter and bracket.

Figure 6:
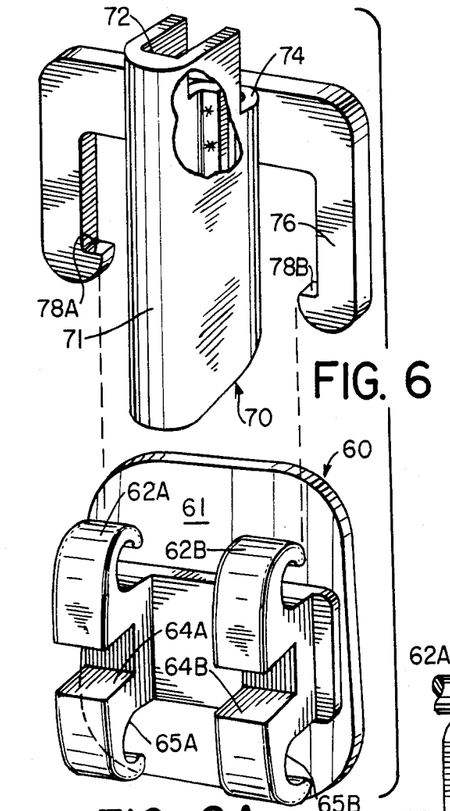
FIG. 6 is an exploded perspective view of the invention shown with a known-type of tooth bracket used in straight wire orthodontic systems.

FIGS. 6 through 8A show a converter which allows the use of light wire orthodontic appliances on straight wire tooth brackets. FIG. 6 shows a typical straight wire tooth bracket 60 having a tooth pad 61 and a pair of substantially parallel vertical bracket flanges 62A and 62B. Bracket flanges 62A and 62B have slots 64A and 64B which retain a rectangular archwire used in straight wire orthodontic treatments. Bracket flanges 62A and 62B also have undersides 65A and 65B.

Figure 8:
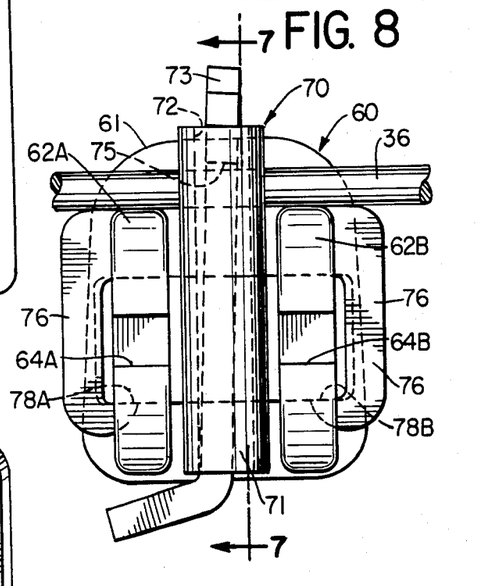
FIG. 8 is a front elevational view of the invention shown installed on a known straight wire-type tooth bracket in conjunction with light wire-type appliances.

Referring to FIG. 6, converter 70 has a body 71 containing a channel 72 adapted for slidable insertion between bracket flanges 62A and 62B. The body has a notch 74 which retains a light wire system archwire between itself and the pad 61 of bracket 60. The converter 70 is attached to bracket 60 by clip means such as c-shaped clip 76. Clip 76 has a pair of lips 78A and 78B which are biased in an inwardly direction when converter 70 slides between bracket flanges 62A and 62B. When converter 70 is inserted onto bracket 60, lips 78A and 78B engage the undersides 65A and 65B of flanges 64A and 64B, to prevent separation of the converter from the bracket. Engagement of lips 78A and 78B with flange undersides 65A and 65B is shown in FIG. 8. An orthodontist may separate converter 70 from bracket 60 by spreading lips 78A and 78B in an outwardly direction while simultaneously lifting the converter.

Figure 8A:
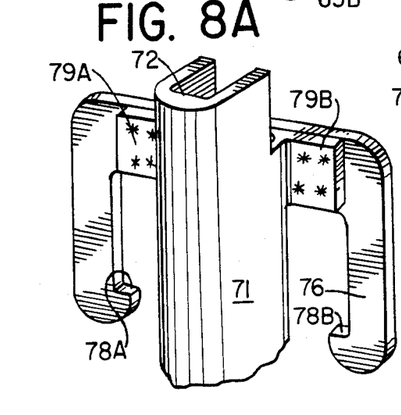
FIG. 8A is a perspective view of an alternate embodiment of the bracket shown in FIG. 6.

FIGS. 6 and 8A show alternative methods for mounting clip 76 to converter body 71. In FIG. 6, the clip 76 is attached to the body by means well known in the orthodontic appliance manufacturing arts, such as soldering or spot welding. In FIG. 8A converter body 71 has ears 79A and 79B to permit welding in a simple manner between body 71 and clip 76. The ears also help to increase rigidity of the clip 76 and body 71 combination.

Figure 7:
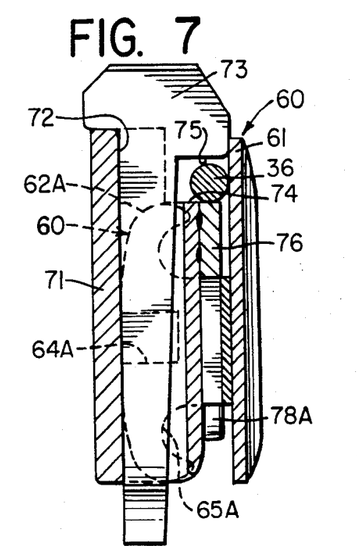
FIG. 7 is a sectional elevational view taken along 7—7 of FIG. 8 showing the converter after installation.

FIGS. 7 and 8 show converter 70 attached to bracket 60 along with insertion of a round archwire 36 used in light wire orthodontic appliances. Arch wire 36 is placed within notch 74. To close the top portion of notch 74 and prevent removal of archwire 36, locking finger 73 is inserted into channel 72 of body 71. Finger 73 has a lug 75 which prevents upward movement of wire 36. To prevent upward vertical movement of locking finger 73, the bottom end of the finger is bent to a locked position by the installing orthodontist. Finger 73 is removed by cutting off the bent end.

Figure 9:
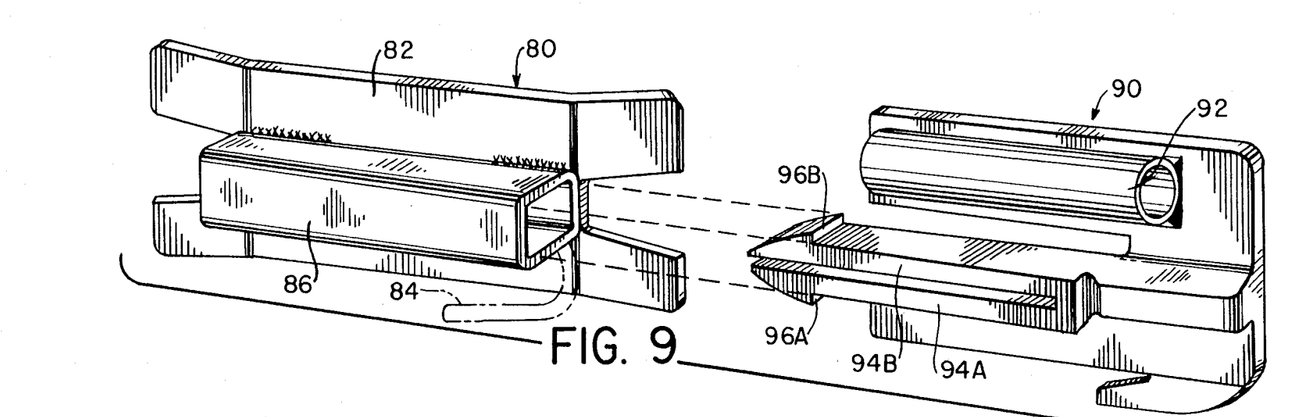
FIG. 9 is an exploded perspective view of another embodiment of the invention prior to insertion into a known-type of molar sheath used in straight wire appliance systems.
Figure 10:
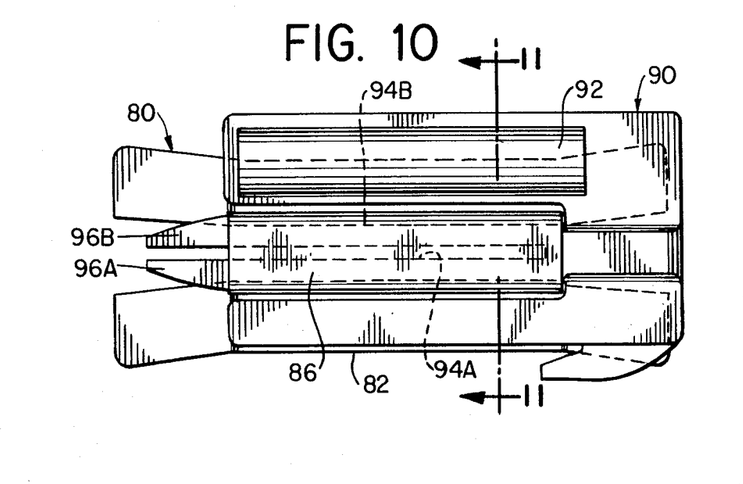
FIG. 10 is a front elevational view after insertion into the molar sheath.
Figure 11:
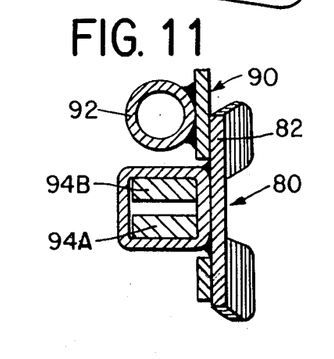
FIG. 11 is a side sectional elevational view taken along line 11—11 of FIG. 10.
Figures 12, 13, 14:
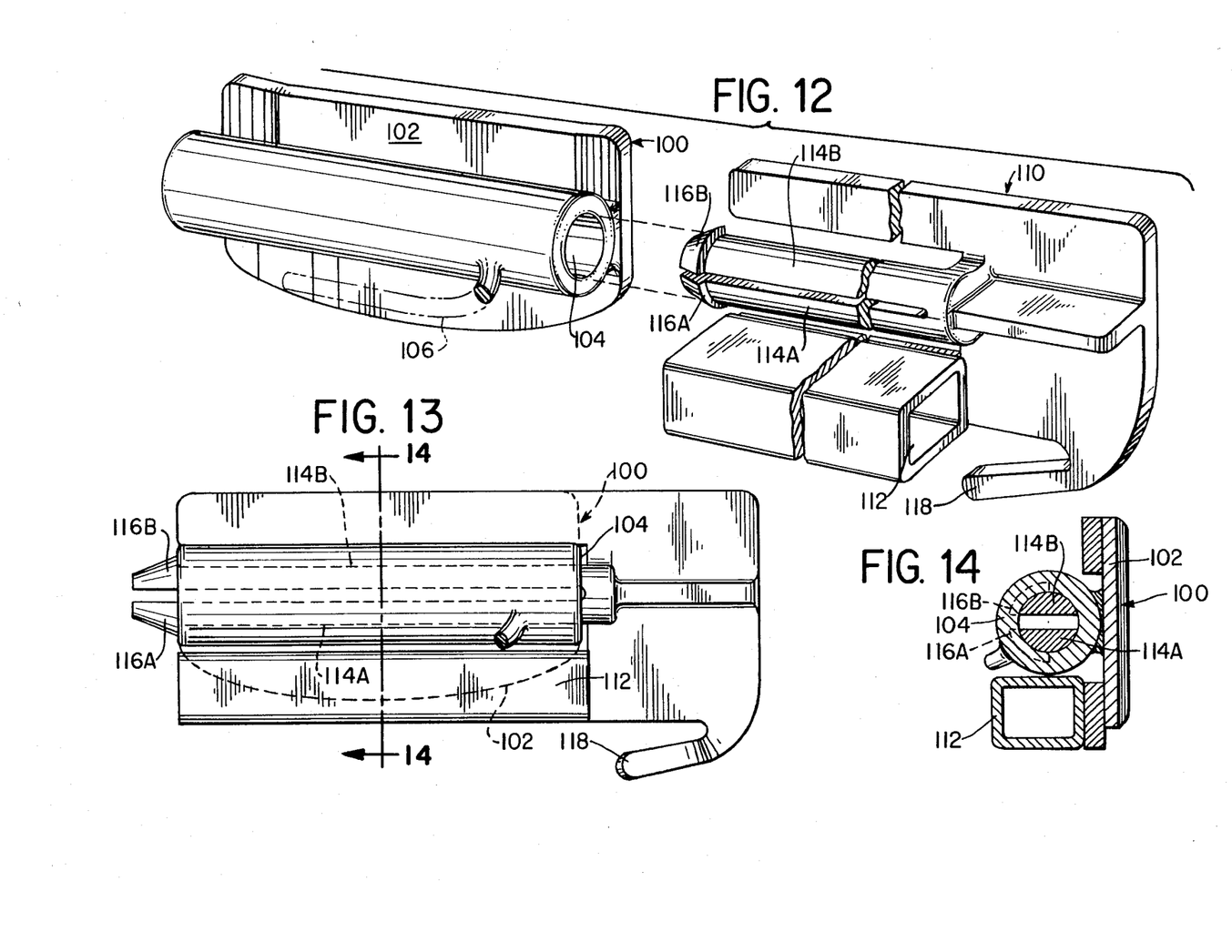
FIG. 12 is an exploded perspective view of another embodiment of the invention shown prior to insertion into a known light wire-type molar buccal tube used in straight wire orthdontic appliance systems.
FIG. 13 is a front elevational view after insertion of the invention into the known light wire-type buccal tube.
FIG. 14 is a side sectional elevational view taken along 14—14 of FIG. 13.

In both the light wire, and straight wire systems, molars have tooth archwire receptacles different from those used on other teeth. They have long, horizontal tubes defining central apertures to accept the archwires. Accordingly, I have developed a different set of converters for use with molar receptacles. FIGS. 9 through 11 show a converter for adapting light wire appliance systems to straight wire molar teeth rectangular sheaths. FIGS. 12 through 14 show a converter for adaption of straight wire appliance systems to light wire molar buccal tubes.

FIG. 9 shows a straight wire molar sheath 80 having pad 82 which is attached to the tooth by methods well known in the orthodontic field, and a rectangular sheath tube for receipt of a rectangular archwire. Appliance attachment means, such as hook 84, are removed by the orthodontist prior to installation of converter 90. The sheath 80 has an aperture or tube 86 to accept a rectangular archwire.

Converter 90 has a tube or aperture 92 adapted for receipt of a light wire-type arch. Clip means, such as clips 94A and 94B slidably insert into tube 86. Lips 96A and 96B prevent separation of converter 90 from sheath 80 once the converter is seated. An orthodontist may selectively remove converter 90 by squeezing lips 96A and 96B in an inwardly direction while simultaneously sliding the clips 94A and 94B from tube 86. FIGS. 10 and 11 show the converter 90 inserted into tube 86. Converter 90 has attachment means such as hook 95.

FIG. 12 shows converter for adapting straight wire molar appliance systems to light wire molar buccal tubes. Light wire buccal tube 100 has a pad 102 for attachment to the molar by means well known in the orthodontic art. It has an aperture or tube 104 for insertion of a light wire-type arch. Hook 106 is removed by the orthodontist prior to insertion of converter 110. Converter 110 has a rectangular aperture 112 for slidable insertion of a rectangular straight wire type arch.

Converter 110 is attached to bracket 100 by clip means such as snap clips 114A and 114B. Lips 116A and 116B prevent separation of the converter 110 from bracket 100 after the converter is seated. An orthodontist may selectively remove converter 110 by squeezing lips 116A and 116B in a radially inwardly direction while simultaneously removing the converter 110. Converter 110 also has attachment means such as hook 118 for elastic or other equipment used in orthodontic appliance systems. FIGS. 13 and 14 show converter 110 inserted onto bracket 100.

It will thus be appreciated from the foregoing, that the converters of my invention facilitate use with the brackets, buccal tubes and sheaths that are presently, commonly, in use, in present day orthodontics, and conversion from one system to another is thereby obviated. Adaptation can be accomplished in minutes in the orthodontist's office, due particularly to the snap clip feature of my invention—for example a patient moves from the east coast to California she has Begg lightwire appliances in place. When this patient selects an orthodontist for continuation of her treatment the selection does not have to be on a basis of the type of bracket system he uses, since the new orthodontist can easily and simply, without discomfort to the patient, convert from Begg to edgewise treatment in less than five minutes or the reverse for a patient moving east from California. Furthermore an orthodontist can start a patient with the Begg system for speed and gentleness then convert to the edgewise straight wire system to detail and fine tune the occlusion a few months before removing the braces.

I claim:

1. An orthodontic converter for adapting a first appliance member associated with an orthodontic treatment system of a first type, for use with an orthodontic treatment system of a second type, the first appliance member having a notch for receipt of an archwire associated with an orthodontic treatment system of the first type, the first appliance member defining a channel and having a peripheral edge at one end thereof, which comprises, a second appliance member having integral clip means formed of a pair of separable flexible snap clip members configured and dimensioned for insertion through the channel so that said snap clip members flex toward each other during insertion through the channel and for snap locking engagement against the peripheral edge so as to provide for selective attachment and detachment to the first appliance member, said second appliance member defining cut-out means for reception of an archwire associated with said second system.

2. An orthodontic converter for adapting a first appliance member associated with an orthodontic treatment system of a first type, for use with an orthodontic treatment system of a second type, the first appliance member being attachable to a tooth, the first appliance member having a notch for receipt of an archwire associated with an orthodontic treatment system of the first type, which comprises a second appliance member having integral clip means for selective attachment and detachment to the first appliance member associated with the orthodontic treatment system of the first type, said second appliance member having a horizontal centerline when attached to the first appliance member, said second appliance member defining cut-out means extending generally across said horizontal centerline for reception of an archwire associated with said second system, such that forces exerted on said second member during orthodontic treatment correspondingly centers the forces substantially along the horizontal centerline, said cut-out means being positioned on said second appliance member such that after attachment of said second appliance member to the first appliance member said cut-out means generally coincides in direction with that of the notch of the first appliance member so that the force by either method of treatment acts along substantially the same line of action.

3. The converter according to claim 1 or claim 2 wherein said second member utilizes a rectangular archwire used in straight wire orthodontic appliance treatment systems and said first member is a tooth archwire receptacle used in light wire orthodontic treatment systems.

4. The converter according to claim 1 or claim 2 wherein said second member utilizes an archwire used in light wire orthodontic appliance treatment systems and said first member is a tooth archwire receptacle used in straight wire orthodontic treatment systems.

5. A converter for attachment to light wire orthodontic appliance tooth archwire receptacles, the receptacle having a channel and having a peripheral edge at one end thereof, wherein said converter comprises:
 (a) integral clip means formed of a pair of separable flexible snap clip members configured and dimensioned for insertion through the channel so that said snap clip members flex toward each other during insertion through the channel and for snap locking engagement against the peripheral edge so as to provide for attachment to the receptacle channel; and
 (b) a slot extending generally horizontally across the converter adapted for reception of a rectangular archwire used in straight wire orthodontic appliance systems, such that the light wire orthodontic system receptacles can be used in straight wire orthodontic treatment.

6. The converter according to claim 5 which comprises:
 (a) reinforcement means attached to the clip means adapted for insertion into said channel for prevention of converter rocking within the bracket channel and for increasing converter strength and tip and torque control.

7. A converter for attachment to light wire orthodontic appliance tooth archwire receptacles, the receptacles having a channel and a receptacle slot in the channel perpendicular to the channel, said converter having:
 (a) integral clip means for attachment to the receptacle channel; and
 (b) a slot extending generally horizontally across the clip means adapted for receipt of a rectangular archwire used in straight wire orthodontic appliance treatment systems, said converter slot being disposed in the receptacle slot, such that the light wire orthodontic system receptacles can be used in straight wire orthodontic treatment, said converter slot being positioned on the converter such that after attachment of said converter to the receptacle said converter slot generally coincides in direction with that of the receptacle slot so that the force by either method of treatment acts along substantially the same line of action.

8. The converter according to claim 7 further comprising:
 (a) reinforcement means attached to the clip means adapted for insertion into the receptacle channel for reducing movement of the inserted converter within the tooth bracket; and
 (b) ribs adapted to abut the channel, said ribs having converter slots corresponding to the converter slots on the clip means for receipt of a rectangular archwire.

9. A converter for attachment to light wire orthodontic appliance tooth archwire receptacles, the receptacles having a channel and a receptacle slot in the channel perpendicular to the channel, said converter having:
 (a) integral snap clip means for attachment to the receptacle channel; and
 (b) a slot extending generally horizontally across the snap clip means adapted for receipt of a rectangular archwire used in straight wire orthodontic appliance treatment systems, said converter slot being disposed in the receptacle slot, such that the light wire orthodontic system receptacles are used in straight wire orthodontic treatment, said converter slot being positioned on the converter such that after attachment of said converter to the receptacle said converter slot generally conincides in direction with that of the receptacle slot so that the force by either method of treatment acts along substantially the same line of action.

10. A converter for attachment to light wire orthodontic system tooth archwire receptacles, the receptacles having an aperture for insertion of an archwire, wherein said converter comprises:
 (a) integral clip means for attachment to the receptacle aperture; and
 (b) a converter aperture adapted for insertion of a rectangular archwire used in straight wire orthodontic systems, such that light wire orthodontic system receptacles can be used in straight wire orthodontic treatment, said converter aperture being positioned on the converter such that after attachment of said converter to the receptacle said converter aperture generally coincides in direction with that of the aperture of the receptacle so that the force by either method of treatment acts along substantially the same line of action.

11. The converter according to any one of claims 1, 2, or 5 wherein the converter has means to receive auxiliary equipment used in orthodontic treatment.

12. A converter for attachment to straight wire orthodontic appliance tooth archwire receptacles, the receptacles having a pair of parallel vertical flanges perpendicular to the receptacle, each flange adapted to receive a rectangular archwire, wherein the converter comprises:
 (a) a body adapted to fit between the parallel flanges of the receptacle, the body having a notch for receipt of a light wire system archwire, and a channel extending generally parallel to the receptacle flanges;
 (b) clip means for clipping the converter to the receptacle flanges; and
 (c) a locking finger having a lug, said locking finger adapted for insertion into the converter channel wherein the finger lug fits over the converter notch and prevents escape of a light wire-type archwire inserted therein; such that straight wire appliance system receptacles are used in light wire orthodontic treatment.

13. A converter for attachment to straight wire orthodontic appliance tooth archwire receptacles, the receptacles having a pair of parallel vertical flanges perpendicular to the receptacle, each flange adapted to receive a rectangular archwire, wherein the converter comprises:
- (a) a body adapted to fit between the parallel flanges of the receptacle, the body having a notch for receipt of a light wire system archwire, and a channel extending generally parallel to the receptacle flanges;
- (b) snap clip means for clipping the converter to the receptacle flanges; and
- (c) a locking finger having a lug, said locking finger adapted for insertion into the converter channel wherein the finger lug fits over the converter notch and prevents escape of a light wire-type archwire inserted therein; such that straight wire appliance system receptacles are used in light wire orthodontic treatment.

14. A converter for attachment to straight wire orthodontic appliance system tooth archwire receptacles having an aperture adapted for receipt of a rectangular archwire, wherein the converter comprises:
- (a) integral clip means adapted for attachment to the receptacle aperture; and
- (b) an aperture adapted for receipt of an archwire used in straight wire orthodontic systems, such that straight wire orthodontic system receptacles can be used in light wire orthodontic treatment, said converter aperture being positioned on the converter such that after attachment of said converter to said receptacle said converter aperture generally coincides in direction with that of the aperture of the receptacle so that the force by either method of treatment acts along substantially the same line of action.

15. The converter according to claim 3, wherein the converter has means to receive auxiliary equipment used in orthodontic treatment.

16. The converter according to claim 4, wherein the converter has means to receive auxiliary equipment used in orthodontic treatment.

17. A converter for attachment to light wire orthodontic appliance tooth archwire receptacles, the receptacle having a channel and having a peripheral edge at one end thereof, wherein said converter comprises:
- (a) integral clip means formed of a pair of separable flexible snap clip members configured and dimensioned for insertion through the channel so that said clip members flex toward each other during insertion through the channel and for snap locking engagement against the peripheral edge so as to provide for attachment to the receptacle channel; and
- (b) a slot extending generally horizontally across the converter adapted for reception of a rectangular archwire used in straight wire orthodontic appliance systems, such that the light wire orthodontic system receptacles can be used in straight wire orthodontic treatment.

* * * * *